United States Patent [19]

Schnepf et al.

[11] Patent Number: 5,702,703
[45] Date of Patent: Dec. 30, 1997

[54] *BACILLUS THURINGIENSIS* TOXIN ENHANCER

[75] Inventors: H. Ernest Schnepf; Brian Stockhoff, both of San Diego; Mark Knuth, Poway, all of Calif.

[73] Assignee: Mycogen Corporation, San Diego, Calif.

[21] Appl. No.: 340,563

[22] Filed: Nov. 16, 1994

[51] Int. Cl.$^6$ .............................. A01N 63/00; C05F 11/08; C12N 1/00
[52] U.S. Cl. .............................. 424/93.461; 424/93.46; 530/350; 530/825; 71/1; 71/6; 435/832; 435/834
[58] Field of Search .............................. 514/12; 530/350, 530/825; 424/93.46, 93.461; 71/1, 6; 435/832, 834

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,797,276 | 1/1989 | Herrnstadt et al. | 424/84 |
| 4,849,217 | 7/1989 | Soares et al. | 424/93 |
| 4,853,331 | 8/1989 | Herrnstadt et al. | 435/257.1 |
| 4,918,006 | 4/1990 | Ellar et al. | 435/69.1 |
| 4,948,734 | 8/1990 | Edwards et al. | 435/252.5 |
| 5,055,294 | 10/1991 | Gilroy | 424/93 |
| 5,128,130 | 7/1992 | Gilroy et al. | 424/934 |
| 5,151,363 | 9/1992 | Payne | 435/252.5 |
| 5,208,017 | 5/1993 | Bradfisch et al. | 424/84 |
| 5,268,297 | 12/1993 | Payne et al. | 435/252.5 |
| 5,298,245 | 3/1994 | Payne et al. | 424/936 |
| 5,302,387 | 4/1994 | Payne et al. | 424/932 |
| 5,352,661 | 10/1994 | Payne et al. | 424/93.2 |
| 5,427,786 | 6/1995 | Payne et al. | 424/93.461 |

FOREIGN PATENT DOCUMENTS 1812092  10/1992  Australia.

OTHER PUBLICATIONS

Gaertner, F.H., L. Kim (1988) "Current Applied Recombinant DNA Projects" TIBTECH 6:S4–S7.

Gaertner, F.H. (1989) "Cellular delivery systems for insecticidal proteins: living and non–living microorganisms" in Controlled Deliver of Crop–Protection Agents, pp. 245–255.

Couch, T.L. (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in AGroecosystems" in Developments in Industrial Microbiology 20:97–104.

Krieg, A. et al. (1983) "*Bacillus thuringiensis* var. *tenebrionis*: ein neuer, gegenuber Larven von Coleopteren Wirksamer Pathotyp" Z. ang. Ent. 96:500–508.

Hofte, H., H.R. Whiteley (1989) "Insecticidal Crystal Proteins of *Bacillus thuringiensis*" Microbiological Reviews 52(2):242–255.

Feitelson, J.S. et al. (1992) "*Bacillus thuringiensis*: Insects and Beyond" Bio/Technology 10:271–275.

Schnepf, H.E., H.R. Whiteley (1981) "Cloning and expression of the *Bacillus thuringiensis* crystal protein gene in *Escherichia coli*" Proc. Natl. Acad. Sci. USA 78(5):2893–2897.

Silo–Suh, L.A. et al. (1994) "biological Activities of Two Fungistatic Antibiotics Produced by *Bacillus cereus* UW85" Applied and Environmental Microbiology 60(6):2023–2030.

*Primary Examiner*—Cecilia J. Tsang
*Assistant Examiner*—Abdel A. Mohamed
*Attorney, Agent, or Firm*—Saliwanchik, Lloyd & Saliwanchik

[57] ABSTRACT

The activity of pesticides is enhanced by application of a zwittermicin antibiotic in combination with insecticides. In particular, zwittermicin enhances the activity of *Bacillus thuringiensis* δ-endotoxins.

11 Claims, No Drawings

BACILLUS THURINGIENSIS TOXIN ENHANCER

BACKGROUND OF THE INVENTION

The present invention relates to the use of a zwittermicin antibiotic to enhance the activity of pesticides. In particular, zwittermicin A and its acetyl derivative (collectively referred to as "zwittermicin") are applied concurrently with a pesticide such as a synthetic chemical and/or a biological pesticide whereby the activity or potency of the pesticide is enhanced. Additionally, the present invention relates to enhanced pesticidal compositions which contain zwittermicin in combination with the pesticide.

Synthetic chemical pesticides are being increasingly scrutinized, and correctly so, for their potential toxic environmental consequences. Synthetic chemical pesticides can poison the soil and underlying aquifers, pollute surface waters as a result of runoff, and destroy non-target life forms. Synthetic chemical control agents have the further disadvantage of presenting public safety hazards when they are applied in areas where pets, farm animals, or children may come into contact with them. Regulatory agencies around the world are restricting and/or banning the uses of many pesticides and particularly the organic synthetic chemical pesticides which are persistent in the environment and enter the food chain. Examples of widely used synthetic chemical pesticides include the organochlorines, e.g., DDT, mirex, kepone, lindane, aldrin, chlordane, aldicarb, and dieldrin; the organophosphates, e.g., chlorpyrifos, parathion, malathion, and diazinon; and carbamates. Because of the problems associated with the use of organic synthetic chemical pesticides, there exists a clear need to limit the use of these agents and a need to identify alternative control agents.

The replacement of synthetic chemical pesticides, or combination of these agents with biological pesticides, could reduce the levels of toxic chemicals in the environment. As used herein, a "biological pesticide" is a naturally occurring, or naturally derived, compound that exhibits toxicity towards insects or other pests such as nematodes, mites, fungi, bacteria, lice, protozoa, and flukes. A biological pesticidal agent that is enjoying increasing popularity is the soil microbe *Bacillus thuringiensis (B.t.)*. *Bacillus thuringiensis* is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for pest resistance and the use of stabilized intact microbial cells as *B.t.* endotoxin delivery vehicles (Gaertner, F. H., L. Kim [1988]TIBTECH 6:S4-S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystal called a δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *tenebrionis* (a.k.a. *B.t.* M-7, a.k.a. *B.t. san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins; ed., Taylor and Francis, New York and London, 1990, pp. 245–255). See also Couch, T. L. (1980) "Mosquito Pathogenicity of *Bacillus thuringiensis* var. *israelensis*, "Developments in Industrial Microbiology 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a *B.t.* crystal protein gene in *Escherichia coli* has been described in the published literature (Sehnepf, H. E., H. R. Whiteley [1981]*Proc. Natl. Acad. Sci. USA* 78:2893–2897). U.S. Pat. No. 4,448,885 and U.S. Pat. No. 4,467,036 both disclose the expression of a *B.t.* crystal protein in *E. coli*. Hybrid *B.t.* crystal protein genes have been constructed that exhibit increased toxicity and display an expanded host range to a target pest. See U.S. Pat. Nos. 5,128,130 and 5,055,294. U.S. Pat. Nos. 4,797,276 and 4,853,331 disclose *B. thuringiensis* strain *san diego* (a.k.a. *B.t. tenebtionis*, a.k.a. M-7) which can be used to control coleopteran pests in various environments. U.S. Pat. No. 4,918,006 discloses *B.t.* toxins having activity against dipterans. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes.

As a result of extensive research and investment of resources, other patents have issued for new *B.t.* isolates and new uses of *B.t.* isolates. The widespread use of *B.t.* isolates is limited by cost of production and limited efficacy on recalcitrant pests. Compounds that augment the pesticidal effects of *B.t.* biopesticides would increase the desirability of these natural products.

Zwittermicin A is a known antibiotic useful as an antifungal agent and plant protection agent. See He et al. (1994) *Tetrahedron Lett.* 35(16):2499–2502; Siloh-Suh et al. (1994) *Appl. Environ. Microbiol.* 60(6):2023–2030; and Australian Patent AU-A-18120/92. Zwittermicin A is derived from *Bacillus cereus*.

The present invention provides a solution to the above-identified problems. Namely, the amounts of chemical pesticide necessary to control pests can be reduced per unit area, thereby reducing exposure of nontargeted organisms such as beneficial insects, mammals, birds, reptiles, amphibians, and fish. Additionally, the activity of biological pesticides can be increased, thereby improving the efficiency of these environmentally friendly pesticides.

BRIEF SUMMARY OF THE INVENTION

Briefly, in accordance with the present invention, zwittermicin is applied concurrently with, or in admixture with, one or more pesticides. The zwittermicin is employed in an amount which enhances the activity of the pesticides.

Of particular importance in the practice of the present invention, zwittermicin is combined with one or more *Bacillus thuringiensis* (*B.t.*) δ-endotoxins in a pesticidal formulation whereby the activity of the *B.t.* toxin is enhanced compared to its activity alone.

DETAILED DISCLOSURE OF THE INVENTION

In practicing the present invention, zwittermicin is applied concurrently with a pesticide whereby the toxic activity of the pesticide is enhanced. The zwittermicin can be applied separately (before or after) from application of the pesticides, or the zwittermicin can be applied in combination with the pesticides by combining the pesticide and zwittermicin in a single pesticidal composition. Thus, as used herein, reference to the concurrent application of these ingredients refers to application such that the two agents can exert their advantageous effects in combination. The zwittermicin is applied in an pesticide-enhancing amount usually at least about 0.00001% by weight of the pesticide, preferably from about 0.0001 to 5 wt. %, and more preferably from about 0.001 to 1 wt. % of the active pesticidal agent. It is preferred to combine the zwittermicin with the pesticide component to form a pesticidal composition which has enhanced pesticidal activity.

The term "zwittermicin" when used herein encompasses both zwittermicin A and its acetyl derivative (zwittermicin Ac), which are known compounds and correspond to the formula:

$$H_2N \overset{O}{\underset{2}{\|}}\underset{H}{\overset{}{N}}\underset{5}{\overset{}{\|}}\underset{}{\overset{}{N}}\underset{6}{\overset{H}{\|}}\underset{7}{\overset{}{N}}\underset{O}{\overset{OR}{\|}}\underset{OR}{\overset{NHR}{\|}}\underset{OR}{\overset{}{\|}}\underset{15}{\overset{NHR}{\|}}OR$$
$$\overset{O}{\|}-NH_2$$

wherein R=H (zwittermicin A) or acetyl (zwittermicin Ac).

Zwittermicin A can be produced by the fermentation of *B. cereus* UW85 ATCC 53522 and isolated as described in He et al., supra, and AU-A-18120/92, both of which are incorporated herein by reference. Zwittermicin Ac can be prepared by reacting zwittermicin A with acetic anhydride in a reaction medium such as, for example, equal parts water and pyridine as described by He et al.

In accordance with the subject invention, zwittermicin is applied in conjunction with one or more pesticides to enhance the pesticidal activity. The zwittermicin is applied at a rate of at least about 0.00001 wt. % based on the weight of the pesticide. Preferably, zwittermicin and one or more *B.t.* pesticides are combined to make a pesticidal composition wherein the *B.t.* has enhanced pesticidal activity. The zwittermicin is added in an amount of at least 0.00001 wt. % of *B.t.*, preferably from about 0.0001 to 1 wt. %, and more preferably from about 0.01 to 0.5 wt. %. Mixtures of zwittermicin A and zwittermicin Ac can also be employed.

Zwittermicin enhances the activity of any pesticide regardless of its mechanism of action. The pesticide can be an organic synthetic chemical pesticide; or a biological pesticide such as azadirachtin, rotenone, pyrethrins, or avermectin; or the δ-endotoxins of *B.t.* as described herein. Mixtures of pesticides can also be employed.

Suitable organic synthetic chemical pesticides include DDT, chlorpyrifos, diazinon, malathion, carbaryl, dimethoate, carbamates, chlordane, aldicarb, organophosphates, pyrethroids, cyanamids, chloronicotinic compounds, halogenated hydrocarbons, and heterocyclic nitroguanidines. Preferred synthetic chemical pesticides include organophosphates, carbamates, and halogenated hydrocarbons.

Among naturally-occurring toxins, i.e., biological pesticides, are the polypeptide crystal toxins of *B. thuringiensis* var. *kurstaki*, active against Lepidoptera; *B. thuringiensis* var. *israelensis*, active against mosquitoes; *B. thuringiensis* var. *aizawai*, active against Spodoptera; and *B. sphaericus*, active against mosquito larvae. Other toxins include those of entomopathogenic fungi, such as beauverin of *Beauveria bassiana* and destruxins of Metarhizium spp.; or the broad spectrum insecticidal compounds, such as the avermectins of *Streptmyces avermitilus*; and the botanicals such as azadirachtin and pyrethrins.

In a preferred embodiment, the biological pesticide comprises *B.t.* δ-endotoxins. The particular *B.t.* employed is not critical. Many *B.t.* toxins have now been discovered and characterized. Höfte and Whiteley classified *B.t.* crystal protein genes into four major classes. The classes were CryI (Lepidoptera-specific), CryII (Lepidoptera- and Diptera-specific), CryIII (Coleoptera-specific), and CryIV (Diptera-specific). Two additional classes have now been identified: CryV (nematode-specific) and CryVI (nematode-specific). The discovery of strains specifically toxic to other pests has been reported. (Feitelson, J. S., J. Payne, L. Kim [1992]*Bio/Technology* 10:271–275). Cultures exemplifying the above are as follows:

*Bacillus thuringiensis* var. *kurstaki* HD-1—NRRL B-3792; disclosed in U.S. Pat. No. 4,448,885;

*Bacillus thuringiensis* var. *israelensis*—ATCC 35646.

The following *B. thuringiensis* cultures are available from the United States Department of Agriculture (USDA) at Brownsville, Tex. Requests should be made to USDA, ARS, Cotton Insects Research Unit, P.O. Box 1033, Brownsville, Tex. 78520 USA; or at the Northern Research Laboratory, U.S. Department of Agriculture, 1815 North University Street, Peoria, Ill., USA.

*B. thuringiensis* HD2
*B. thuringiensis* var. *finitimus* HD3
*B. thuringiensis* var. *alesti* HD4
*B. thuringiensis* var. *kurstaki* HD73
*B. thuringiensis* var. *sotto* HD770
*B. thuringiensis* var. *dendrolimus* HD7
*B. thuringiensis* var. *kenyae* HD5
*B. thuringiensis* var. *galleriae* HD29
*B. thuringiensis* var. *canadensis* HD224
*B. thuringiensis* var. *entomocidus* HD9
*B. thuringiensis* var. *subtoxicus* HD109
*B. thuringiensis* var. *aizawai* HD11
*B. thuringiensis* var. *morrisoni* HD12
*B. thuringiensis* var. *ostriniae* HD501
*B. thuringiensis* var. *tolworthi* HD537
*B. thuringiensis* var. *darmstadiensis* HD146
*B. thuringiensis* var. *toumanoffi* HD201
*B. thuringiensis* var. *kyushuensis* HD541
*B. thuringiensis* var. *thompsoni* HD542
*B. thuringiensis* var. *pakistani* HD395
*B. thuringiensis* var. *israelensis* HD567
*B. thuringiensis* var. *indiana* HD521
*B. thuringiensis* var. *dakota*
*B. thuringiensis* var. *tohokuensis* HD866
*B. thuringiensis* var. *kumanotoensis* HD867
*B. thuringiensis* var. *tochigiensis* HD868
*B. thuringiensis* var. *colmeri* HD847

*B. thuringiensis* var. *wuhanensis* HD525
*B. thuringiensis* var. *bui bui*
*Bacillus cereus*—ATCC 21281
*Bacillus moritai*—ATCC 21282
*Bacillus popilliae*—ATCC 14706
*Bacillus lentimorbus*—ATCC 14707
*Bacillus sphaericus*—ATCC 33203
*Beauveria bassiana*—ATCC 9835
*Metarrhizium anisopliae*—ATCC 24398
*Metarrhizium flavoviride*—ATCC 32969
*Streptomyces avermitilus*—ATCC 31267

The following United States Patents disclose pesticidal *B.t.* isolates or recombinant microbes which express a *B.t.* toxin: U.S. Pat. Nos. 5,006,335; 5,106,620; 5,045,469; 5,135,867; 4,990,332; 5,164,180; 5,126,133; 5,093,119; 5,208,017; 5,186,934; 5,185,148; 5,211,946; 4,948,734; 4,849,217; 4,996,155; 4,999,192; 4,966,765; 5,073,632; 5,196,342; 5,063,055; 5,080,897; 5,024,837; 5,147,640; 5,173,409; and 5,186,934.

*B.t.* toxins can be made available to the target pest by exposing the target pest to wild-type *B.t.* which naturally express the toxin. Alternatively, a gene encoding a desired toxin can be transformed into and expressed in a suitable recombinant host. Fragments of the *B.t.* toxins which retain insecticidal activity can also be used.

In one embodiment of the present invention, zwittermicin A is added to a *B.t.* biopesticide formulation in amount of 0.01% by weight of the formulation. The pesticidal activity of the *B.t.* is enhanced. For example, zwittermicin A is added to the following commercial *B.t.* formulations:

1. MVP®(Mycogen) 99.99%
   zwittermicin A 0.01%
2. DIPEL (Abbott) 99.99%
   zwittermicin A 0.01%
3. XENTARI (Abbott) 99.99%
   zwittermicin A 0.01%
4. AGREE (Ciba-Geigy) 99.99%
   zwittermicin A 0.01%

MVP® contains a CryIA(c) *Bacillus thuringiensis* toxin as the active ingredient. DIPEL contains CryIA(a), CryIA(b), CryIA(c), and CryIIA *Bacillus thuringiensis* toxins as the active ingredients. XENTARI contains CryIA(a), CryIA(b), CryIC, and CryID *Bacillus thuringiensis* toxins as the active ingredients. AGREE contains CryIA(a), CryIA(c), CryIC, and CryID *Bacillus thuringiensis* toxins as the active ingredients.

In another embodiment, zwittermicin can be employed to enhance the activity of *B.t.*-transformed plants. A plant that has been transformed with a functional *B.t.* structural gene to impart pest resistance to the plant can be further protected by applying zwittermicin to the plant surface. The zwittermicin enhances the activity of the *B.t.* inside the plant cells when pests feed on the transformed plant. Because the exact amount of *B.t.* protein present in plant tissues cannot be accurately determined in field applications, for this embodiment the zwittermicin is applied to the plant surface by foliar application. A foliar spray will typically contain at least about 1 ppm and preferably at least about 100 ppm based on the total weight of the foliar spray.

In another embodiment of the present invention, zwittermicin A is mixed with water and any desired agriculturally acceptable adjuvants such as, for example, inert materials, various surface active agents (including artionic, cationic, and non-ionic compounds), preservatives, antifoam agents, binders, emulsifiers, buffers, spreaders, stickers, penetrants, spray oils, and the like. The concentration of zwittermicin will be from about 0.1–10,000 ppm. The composition is then sprayed on plants that have functioning *B.t.* structural gene (s) to enhance the pesticidal activity of the *B.t.* protein.

Zwittermicin A is an amorphous ninhydrin-positive powder and is stable under both neutral and acidic conditions. Zwittermicin A is hydrolyzed under basic conditions into a cyclic byproduct. Zwittermicin Ac also forms a cyclic byproduct under basic conditions. Therefore, any formulations containing zwittermicin should be pH adjusted, if necessary, to prevent degradation of the zwittermicin.

Testing for enhanced pesticidal activity. A qualitative bioassay procedure can be used to detect the pesticide-enhancing activity of zwittermicin with *B.t.* δ-endotoxins (*B.t.*). The procedure consists of testing one or more rates of the zwittermicin in combination with *B.t.* and *B.t.* alone. Enhanced pesticidal activity is evidenced by enhancement of the *B.t.* activity in combination with zwittermicin, as compared to activity of *B.t.* alone.

Bioassay. A dilution of *Bacillus thuringiensis* or recombinant *Pseudomonas fluorescens* (stabilized by the methods disclosed in U.S. Pat. Nos. 4,695,455 and 4,695,462) is divided into two equal parts. To the first part, no changes are made. To the second part, a measured amount of zwittermicin is added. Each of the preparations is mixed with modified USDA soy flour insect diet (Technical Bulletin 1528, U.S. Department of Agriculture). This mixture is poured into plastic trays with compartmentalized 3-ml wells (Nutrend Container Corporation, Jacksonville, Fla.). Distilled water serves as an untreated control as well as the vehicle to introduce the test materials into the diet. Second-instar *Spodoptera exigua* larvae are placed singly onto the diet mixture. Wells then are covered with "MYLAR" sheeting (ClearLam Packaging, Ill.) using a tacking iron. Several pinholes are made into each "MYLAR" well cover to provide gas exchange. Larvae are subjected to continuous light at 25° C. or 29° C. Mortality is recorded after six or four days, respectively. The *B.t.* alone, *B.t.* with zwittermicin, and water control are tested simultaneously. Results are then observed and the pesticidal activity calculated.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of enhancing the activity of a pesticide which comprises applying the pesticide in combination with zwittermicin A, zwittermicin Ac, or mixtures thereof in pesticidal-enhancing amounts.

2. The method, according to claim 1, wherein the pesticide is applied in combination with zwittermicin A.

3. The method, according to claim 1, wherein the pesticide is a biological insecticide.

4. The method, according to claim 3, wherein the biological insecticide is selected from the group consisting of a *Bacillus thuringiensis* δ-endotoxin, rotenone, a pyrethrin, avermectin, azadirachtin, and mixtures thereof.

5. The method, according to claim 4, wherein the biological insecticide is a *Bacillus thuringiensis* δ-endotoxin.

6. The method, according to claim 5, wherein the *Bacillus thuringiensis* δ-endotoxin is selected from the group consisting of CryI, CryII, CryIII, CryIV, CryV, and CryVI, and fragments thereof which retain insecticidal activity.

7. A pesticidal composition which comprises components (a), (b), and (c); wherein component (a) is a pesticide;

component (b) is selected from the group consisting of a pesticidal-enhancing amount of zwittermicin A, zwittermicin Ac, or mixtures thereof; and component (c) is an agriculturally acceptable formulation.

8. The composition, according to claim 7, wherein the pesticide is a biological insecticide.

9. The composition, according to claim 8, wherein the biological insecticide is a *Bacillus thuringiensis* δ-endotoxin.

10. The composition, according to claim 9, wherein the *Bacillus thuringiensis* δ-endotoxin is selected from the group consisting of CryI, CryII, CryIII, CryIV, CryV, and CryVI, and fragments thereof which retain insecticidal activity.

11. The composition, according to claim 10, wherein component (b) is zwittermicin A.

* * * * *

UNITED STATES PATENT AND TRADEMARK OFFICE
CERTIFICATE OF CORRECTION

PATENT NO. : 5,702,703
DATED : December 30, 1997
INVENTOR(S) : H. Ernest Schnepf, et. al.

It is certified that error appears in the above-identified patent and that said Letters Patent is hereby corrected as shown below:

Column 2, line 7: "Wilkins;" should read --Wilkins,--;

line 31: "(Sehnepf," should read --(Schnepf,--; and line 39: "*tenebtionis*" should read --*tenebrionis*--.

Column 4, line 16: "*Streptmyces*" should read --*Streptomyces*--.

Column 5, line 64: "artionic," should read --anionic,--.

Signed and Sealed this

Seventh Day of April, 1998

Attest:

BRUCE LEHMAN

Attesting Officer      *Commissioner of Patents and Trademarks*